United States Patent
Boyle et al.

(10) Patent No.: US 10,111,019 B2
(45) Date of Patent: Oct. 23, 2018

(54) SOUND PROCESSOR MODULE

(71) Applicant: ADVANCED BIONICS AG, Staefa (CH)

(72) Inventors: Patrick Joseph Boyle, Kent (GB); Volkmar Hamacher, Hannover (DE)

(73) Assignee: Advanced Bionics AG, Staefa (CH)

( * ) Notice: Subject to any disclaimer, the term of this patent is extended or adjusted under 35 U.S.C. 154(b) by 116 days.

(21) Appl. No.: 15/323,068

(22) PCT Filed: Jul. 28, 2014

(86) PCT No.: PCT/EP2014/066158
§ 371 (c)(1),
(2) Date: Dec. 29, 2016

(87) PCT Pub. No.: WO2016/015744
PCT Pub. Date: Feb. 4, 2016

(65) Prior Publication Data
US 2018/0176702 A1 Jun. 21, 2018

(51) Int. Cl.
*H04R 25/00* (2006.01)
*A61N 1/36* (2006.01)

(52) U.S. Cl.
CPC ....... *H04R 25/606* (2013.01); *A61N 1/36036* (2017.08); *A61N 1/36038* (2017.08);
(Continued)

(58) Field of Classification Search
CPC .. H04R 25/606; H04R 25/405; H04R 25/407; H04R 2225/021; H04R 2225/67; A61N 1/36038; A61N 1/36036
(Continued)

(56) References Cited

U.S. PATENT DOCUMENTS 6,597,793 B1 * 7/2003 Darbut .............. H04R 25/402
381/313
7,167,572 B1 * 1/2007 Harrison ........... H04R 25/456
381/326
(Continued)

FOREIGN PATENT DOCUMENTS

DE 19852758 5/2000
WO WO-2005/110530 11/2005
(Continued)

OTHER PUBLICATIONS

International Search Report and Written Opinion received in International Application No. PCT/EP2014/066158, dated Mar. 23, 2015.

*Primary Examiner* — Oyesola C Ojo
(74) *Attorney, Agent, or Firm* — ALG Intellectual Property, LLC

(57) ABSTRACT

A behind-the-ear sound processor module includes a BTE-housing; an adjustable microphone module attached to the BTE-housing for capturing input audio signals from ambient sound; and a sound processor unit for generating, from the input audio signals, a neural hearing stimulation signal to be supplied to an implantable neural stimulation arrangement, wherein the microphone module comprises a plurality of microphones and a support element for carrying the microphones, wherein the support element is movable between a beamformer position enabling the plurality of microphones to act as a directional microphone array in a beamformer audio signal processing mode of the sound processor unit and a T-Mic position enabling at least one of the microphones to act as a T-Mic in a T-Mic audio signal processing mode of the sound processor unit at a position closer to the entrance of the ear canal than in the beamformer position.

27 Claims, 3 Drawing Sheets

(52) U.S. Cl.
CPC ......... *H04R 25/405* (2013.01); *H04R 25/407* (2013.01); *H04R 2225/021* (2013.01); *H04R 2225/67* (2013.01)

(58) Field of Classification Search
USPC ........................................................ 381/313
See application file for complete search history.

(56) References Cited

U.S. PATENT DOCUMENTS

| | | | | |
|---|---|---|---|---|
| 7,953,241 | B2* | 5/2011 | Jorgensen | H04R 1/406 381/322 |
| 8,442,245 | B2* | 5/2013 | Wurzbacher | H04R 25/305 381/313 |
| 2004/0028252 | A1* | 2/2004 | McSwiggen | H04R 25/00 381/322 |
| 2005/0251225 | A1* | 11/2005 | Faltys | A61N 1/37229 607/57 |
| 2007/0016267 | A1* | 1/2007 | Griffin | A61N 1/36032 607/57 |
| 2011/0116669 | A1* | 5/2011 | Karunasiri | H04R 25/554 381/330 |
| 2013/0208929 | A1* | 8/2013 | Dittberner | H04R 25/40 381/313 |
| 2015/0281855 | A1* | 10/2015 | Merks | H04R 25/402 381/313 |

FOREIGN PATENT DOCUMENTS

| | | |
|---|---|---|
| WO | WO-2008/010716 | 1/2008 |
| WO | WO-2011/032021 | 3/2011 |
| WO | WO-2011/059924 | 5/2011 |
| WO | WO-2013/101088 | 7/2013 |

* cited by examiner

SOUND PROCESSOR MODULE

The invention relates to a behind-the-ear (BTE) sound processor module for use in a device for neural stimulation of a patient's hearing, such as a cochlear implant (CI) device.

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles.

Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g. CI systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted into the patient's cochlea. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Typically, the audio signal, usually captured by a microphone, is divided into a plurality of analysis channels, each containing a frequency domain signal representative of a distinct frequency portion of the audio signal, wherein the frequency domain signal in each analysis channel may undergo signal processing, such as by applying channel-specific gain to the signals. The processed frequency domain signals are used for generating certain stimulation parameters according to which the stimulation signals for each stimulation channel are generated. The analysis channels are linked to the stimulation channels via channel mapping. The number of stimulation channels may correspond to the number of analysis channels, or there may be more stimulation channels than analysis channels, or there may be more analysis channels than stimulation channels. Various stimulation strategies are used, such as current steering stimulation (in order to stimulate a stimulation site located in between areas associated with two or more electrodes) and n-of-m stimulation (wherein stimulation current is only applied to n of m total stimulation channels during a particular stimulation frame).

An example for such a CI system with electrical cochlea stimulation is described in WO 2011/032021 A1.

Acoustic beamforming relates to methods of providing a plurality of typically omnidirectional microphones with a directional/polar pattern by applying appropriate signal processing to the audio signals captured by the microphones, wherein the mutual distance of the microphones is utilized. Typically, hearing aids and auditory prostheses are provided with such beamforming capability in order to enhance the signal-to-noise ratio of the desired audio signals.

US 2007/0016267 A1 relates to a CI device comprising a plurality of microphones disposed on the BTE sound processor housing, the headpiece housing and/or the cable connecting the sound processor and the headpiece, in order to realize an acoustic beamformer arrangement.

Most CI systems have a built-in microphone located on the housing of the BTE sound processor, or on the headpiece that communicates with the implanted part. However, since the positioning of the headpiece usually is optimized with regard to the transcutaneous signal transmission to the implanted part of the system, the position of the microphone is not normally optimal for picking up sound waves. Therefore, it is popular to use in addition an external microphone which is placed within the concha of the ear near the entrance of the ear canal; such location is ideal because it corresponds to the location where sound is naturally collected by the concha. Such a type of external microphone is commonly known as a "T-Mic" microphone, where "T-Mic" is a registered trademark of Advanced Bionics, AG. Typically, the T-Mic is held in its desired position by a boom or stalk which is attached to the ear hook of the BTE sound processor. An example of such a CI comprising a T-Mic is described in WO 2011/059924 A1.

WO 2008/010716 A2 relates to a hearing aid comprising a BTE module and an in-the-ear (ITE) part connected to the BTE module, wherein the ITE part is provided with a microphone and a loudspeaker and wherein the BTE module may comprise one or more microphones. Similarly, U.S. Pat. No. 8,526,653 B2 relates to a BTE hearing aid comprising a loudspeaker to be placed in the ear canal and a microphone to be placed at the entrance of the ear canal.

The use of a T-Mic is beneficial in many listening situations, since it utilizes the external ear's anatomy to achieve some shielding of sounds from the rear and the enhancement of important speech frequencies; further, it allows natural—and thus convenient—use of telephone devices.

However, in other listening situations, in particular for one-to-one listening in noisy environments, the use of a tight beamformer arrangement could also be of great benefit. However, the size and orientation of today's cochlear implant sound processors limits the separation available for microphones and hence their physical ability to produce a beamformer.

It is an object of the invention to provide for a BTE sound processor module enabling optimized picking-up of sound in different listening situations.

According to the invention, this object is achieved by a sound processor module as defined in claim 1.

The invention is beneficial in that, by providing the BTE sound processor module with an adjustable microphone module which is movable between a beamformer position, enabling a plurality of microphones to act as a directional microphone array, and a T-Mic position enabling at least one of the microphone to act as a T-Mic in a position closer to the entrance of the ear channel than in the beam former position, the sound pick-up process can be optimized for the respective listening situation: the beamformer position of the microphone module may be used in situations in which beamforming is particularly beneficial, and the T-Mic position may be used in situations in which the use of a T-Mic is particularly beneficial.

Further, such microphone position-driven switching of the sound pick-up mode is particularly easy also for users with limited dexterity or vision, since it only requires handling of a—typically relatively large microphone module—rather than operation of e.g. small switches or buttons.

Moreover, by providing an adjustable microphone module, the limitations of the sound processor housing with regard to the placement of microphones suitable forming a beamforming array can be overcome, since the microphone module allows a placement of the microphones without the usual constraints resulting from size, geometry and placement of the sound processor housing. Thus a beamformer with enhanced performance may be realized.

Also, moving the microphones outside the sound processor module housing provides for additional benefits: for example, the microphone module may be replaced in case of damage or degradation, without the need to replace the entire sound processor module; further, system flexibility can be enhanced, since the microphone module may be provided as a performance upgrade of a more simple basic sound processor module, including simplification of the management of stock (typically, the microphones are likely to be a weak point of the sound processor module).

Preferred embodiments of the invention are defined in the dependent claims.

Hereinafter, examples of the invention will be illustrated by reference to the attached drawings, wherein.

Figure 1:
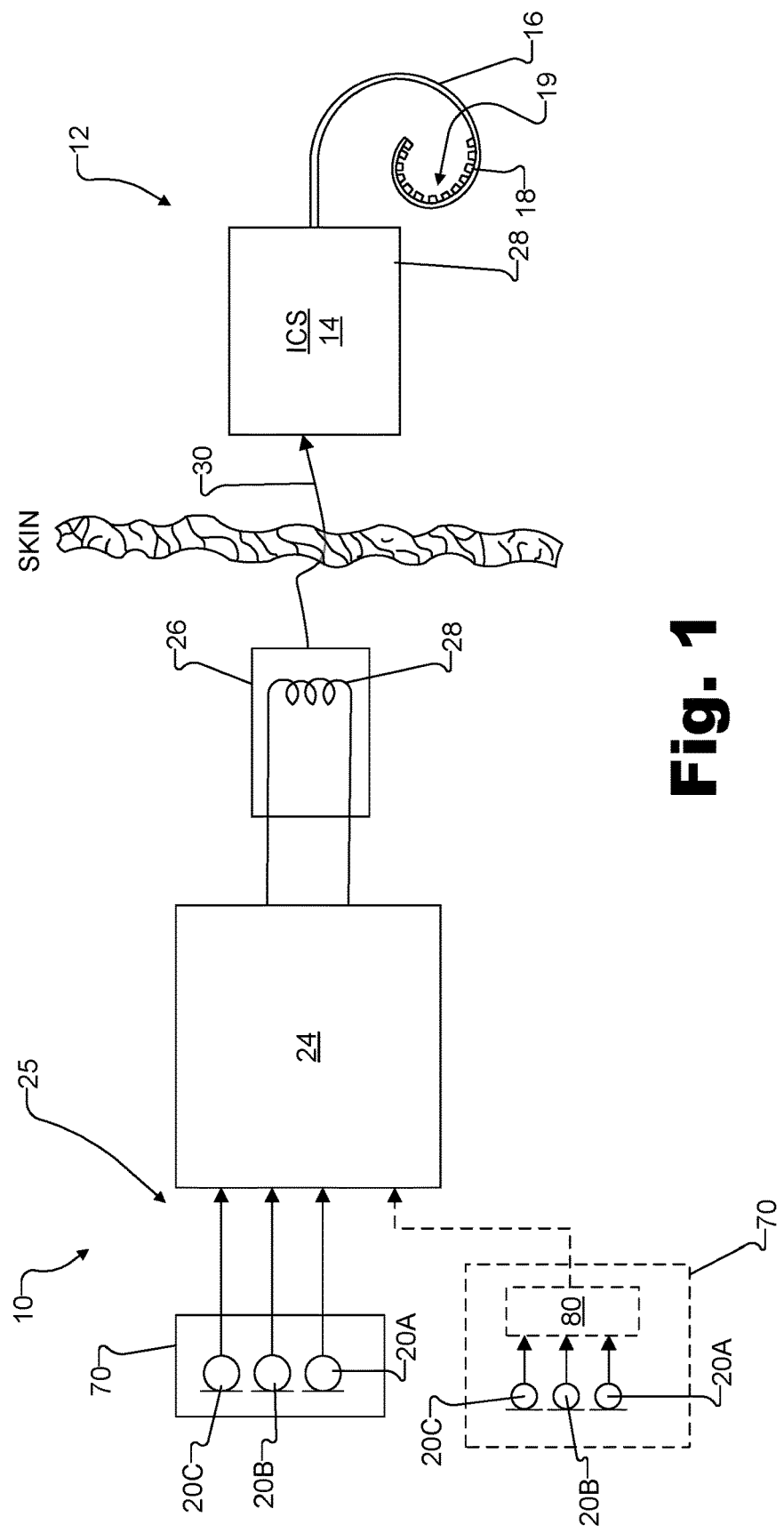
FIG. 1 is a schematic representation of an example of a CI system according to the invention.

In FIG. 1 an example of a cochlear implant system is shown schematically. The system comprises a sound processing sub-system 10 and a stimulation sub-system 12. The sound processing sub-system 10 serves to detect or sense an audio signal and divide the audio signal into a plurality of analysis channels each containing a frequency domain signal (or simply "signal") representative of a distinct frequency portion of the captured audio. A signal level value is determined for each analysis channel by analyzing the respective frequency domain signal. Stimulation parameters are generated based on the frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlea of a patient in accordance with the stimulation parameters received from the sound processing sub-system 10. Electrical stimulation is provided to the patient via a CI stimulation assembly 18 comprising a plurality of stimulation channels, wherein various known stimulation strategies, such as current steering stimulation or N-of-M stimulation, may be utilized.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), duty cycle, spectral tilt, ramp on time, and ramp off time of the stimulation current that is applied to the stimulation site.

Sound processing subsystem 10 and stimulation subsystem 12 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front- and back-end dynamic range parameters, current steering parameters, amplitude values, pulse rate values, pulse width values, polarity values, filter characteristics, and/or any other control parameter as may serve a particular application.

In the example shown in FIG. 1, the stimulation sub-system 12 comprises an ICS 14, a lead 16 and the stimulation assembly 18 disposed on the lead 16. The stimulation assembly 18 comprises a plurality of "stimulation contacts" 19 for electrical stimulation of the auditory nerve. The stimulation assembly 18 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 1, the sound processing sub-system 10 comprises a microphone module 70 including a plurality of microphones 20A, 20B, 20C for capturing audio signals from ambient sound, a sound processor unit 24 which receives audio signals from the microphones 20A, 20B, 20C, and a headpiece 26 having a coil 28 disposed therein. The sound processor unit 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 1 the sound processor unit 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor unit 24 may be implanted and directly connected by wires with the ICS 14, with the microphone module 70 remaining outside; in this case, an implantable microphone may be provided in addition to the microphone module 70.

The sound processor unit 24 and the microphone module 70 together form part of a sound processor module 25 to be worn behind the ear, as will be explained hereinafter in more detail by reference to FIGS. 3 and 4.

Figure 2:
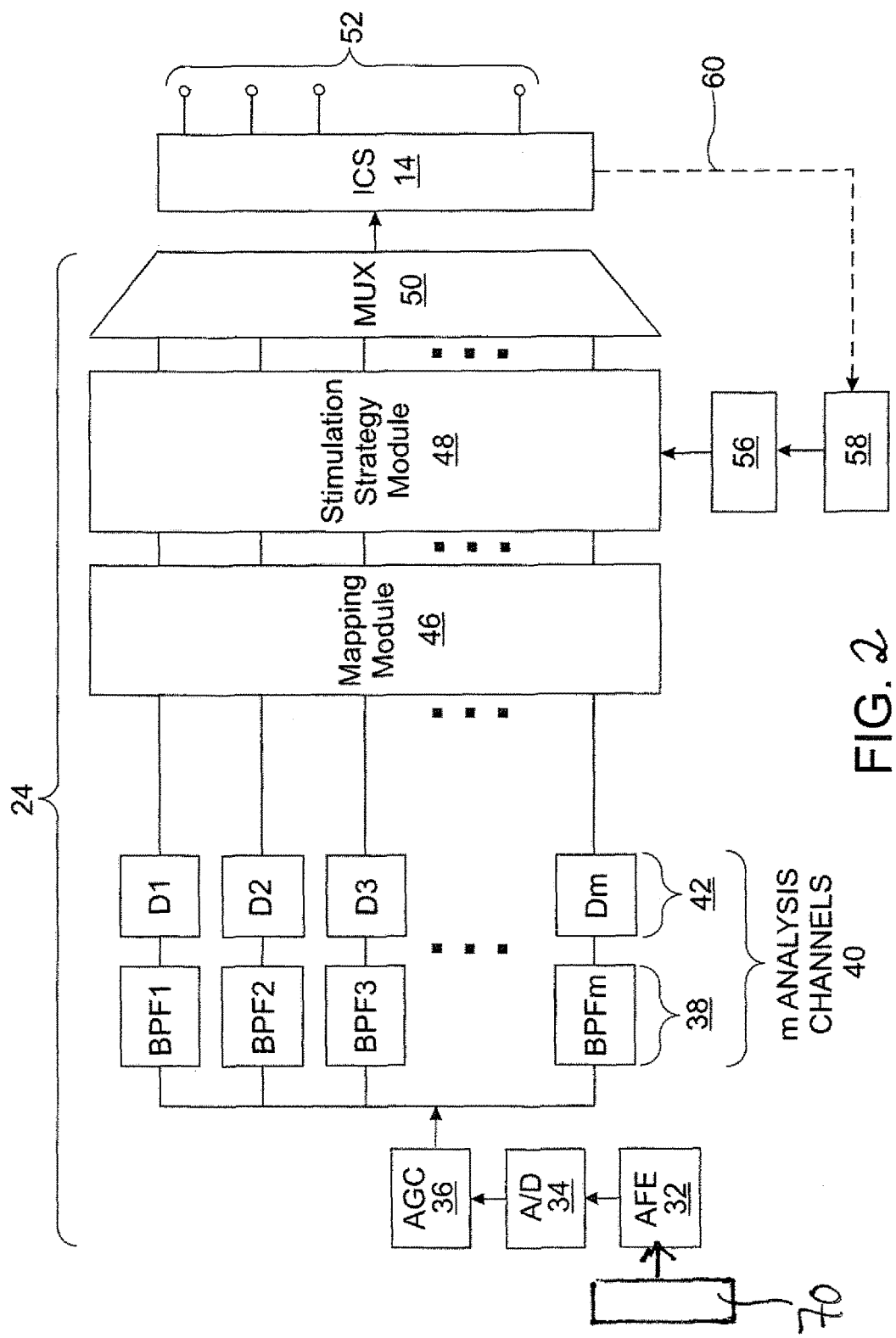
FIG. 2 is a block diagram of an example of the signal processing structure of a CI system according to the invention.

In FIG. 2 a schematic example of a sound processor unit 24 is shown. The audio signals captured by the microphone module 70 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone module 70. For example, such frequency filtering may be implemented by applying a Discrete Fourier Transform to the audio signal and then arranging the resulting frequency bins into the analysis channels 40.

The signals within each analysis channel 40 are input into an envelope detector 42 in order to determine the amount of energy contained within each of the signals within the analysis channels 40 The output signals of the envelope detectors 42 are supplied to a mapping module 46 which serves to map the signals in the analysis channels 40 to the stimulation channels S1 . . . Sn. For example, signal levels may be mapped to amplitude values used to define the electrical stimulation pulses that are applied to the patient by the ICS 14 via M stimulation channels 52. For example, each of the m stimulation channels 52 may be associated to one of the stimulation contacts 19 (FIG. 1) or to a group of the stimulation contacts 19.

The sound processor unit 24 further comprises a stimulation strategy module 48 which serves to generate one or more stimulation parameters based on the signals in the analysis channels 40 and in accordance with a certain stimulation strategy (which may be selected from a plurality of stimulation strategies). For example, stimulation strategy module 48 may generate stimulation parameters which direct the ICS 14 to generate and concurrently apply weighted stimulation currents via a plurality 52 of the stimulation channels S1 . . . Sn in order to effectuate a current steering stimulation strategy. Additionally, or alternatively, the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor unit 24 also comprises a multiplexer 50 which serves to serialize the stimulation parameters generated by the stimulation strategy module 48 so that they can be transmitted to the ICS 14 via the communication link 30, i.e. via the coil 28.

The sound processor unit 24 may operate in accordance with at least one control parameter, such as the most comfortable listening current levels (MCL), also referred to as "M levels", threshold current levels (also referred to as "T levels"), dynamic range parameters, channel acoustic gain parameters, front- and back-end dynamic range parameters, current steering parameters, amplitude values, pulse rate values, pulse width values, polarity values and/or filter characteristics. Examples of such auditory prostheses, as described so far, can be found, for example, in WO 2011/032021 A1.

Figure 3:
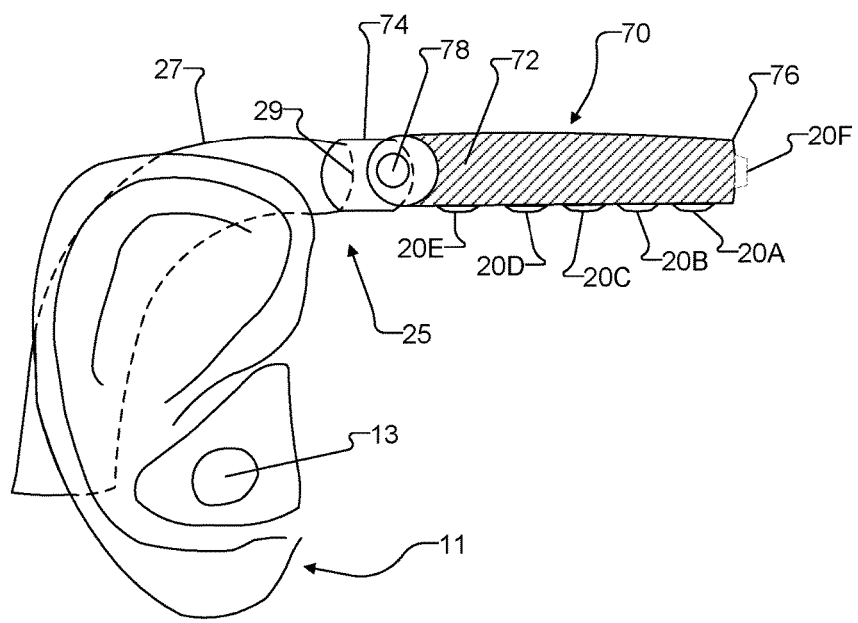
FIG. 3 is a schematic side view of an example of a sound processor module according to the invention when placed at the ear of a patient, with the microphone module being shown in a beamformer position.
Figure 4:
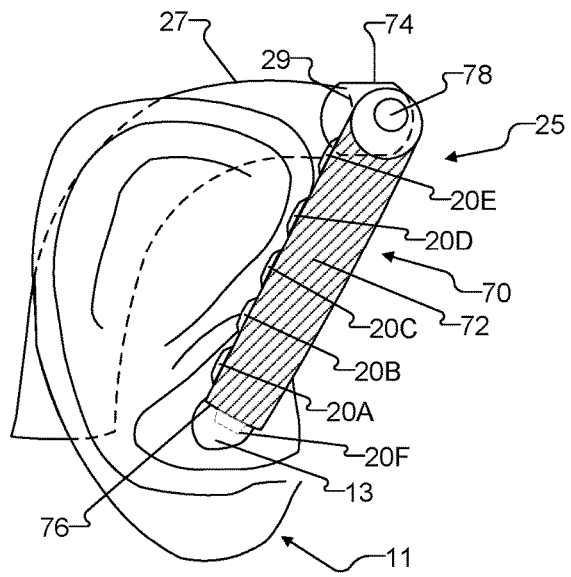
FIG. 4 is a view like FIG. 3, with the microphone module being shown in a T-Mic position.

A schematic example of a BTE sound processor module 25 when worn at an ear 11 of a patient is shown in FIGS. 3 and 4. The sound processor module 25 comprises a BTE housing 27 to be worn behind the ear 11 and a microphone module 70 attached to the BTE housing 27, for example via an adaptor 74. The use of such adaptor 74 allows to retrofit/upgrade products wherein the sound processor module did not include such adjustable microphone module 70. The microphone module 70 comprises a plurality of microphones 20A to 20E which may be arranged, for example, as a linear array. The microphone assembly 70 preferably is designed as an ear hook.

The microphone module 70 comprises a support element 72 for carrying the microphones 20A to 20E, which is preferably designed as an arm having one free end 76 and one end connected to a joint 78 fixed at an upper end 29 of the BTE housing 27 (in the example of FIGS. 3 and 4, the joint 78 is fixed at the upper end 29 via the adaptor 74).

The support element 72 is movable between a beamformer position enabling the microphones 20A to 20E to act as a directional microphone array in a beamformer audio signal processing mode of the sound processor unit 24 and a T-Mic position enabling at least one of the microphones 20A to 20E to act as a T-Mic in a T-Mic audio signal processing mode of the sound processor unit 24, with the at least one microphone acting as the T-Mic being located in the T-Mic position of the microphone module 70 in a position closer to the entrance 13 to the ear canal than in the beamformer position of the microphone module 70. In the example of FIGS. 3 and 4, the support element 72 is pivotable around the joint 78 in a plane substantially parallel to the pinna 11.

In FIG. 3, the microphone module 70 is shown in the beamformer position, whereas in FIG. 4 it is shown in the T-Mic position. In the beamformer position, the microphones 20A to 20E preferably are arranged in a substantially horizontal plane, e.g. having a deviation of less than 20° from the horizontal direction. Preferably, the microphones 20A to 20E are oriented "downwardly" in the beamformer position in order to provide some mechanical protection to the microphones 20A to 20E, such as from rain, i.e. the microphones 20A to 20E are located at that side of the support element 72 which faces the floor in the beamformer position and the microphone membranes are in a substantially horizontal plane (i.e. parallel to the floor). In the T-Mic position the microphones 20A to 20E preferable are arranged in a substantially vertical plane, e.g. having a deviation of less than 30° from the vertical direction.

Preferably, only the microphone closest to the free end 76 of the support element 72, i.e. the microphone 20A, or only the two microphones closest to the free end 76, i.e. the microphones 20A and 20B, are active in the T-Mic mode in order to act as the T-Mic. Typically, the at least one microphone 20A (or 20A and 20B) acting as the T-Mic is located at the entrance 13 of the ear canal in the T-Mic position of the support element 72 (typically, the free end 76 of the support element 72 is located close to the entrance 13 of the ear canal in the T-Mic position (see FIG. 4)).

According to a variant, the at least one microphone acting as the T-Mic may be oriented in an axial direction of the support element 72, as indicated by dashed lines at 20F, rather than being oriented in a transverse direction with regard to the support element 72 (as the microphones 20A to 20E in FIG. 3). As can be seen in FIG. 3, such axial microphone 20F would be oriented "horizontally" in the beamformer mode, i.e. the microphone membrane would be in a substantially vertical plane.

Due to the essentially horizontal orientation of the microphones 20A to 20E in FIG. 3, a directional characteristic/polar pattern can be achieved in a substantially horizontal plane by appropriate signal processing.

According to one embodiment, the microphone module 70 includes circuitry 80 for combining the output signals of the microphones 20A to 20E according to a beamforming algorithm in order to supply a beamformer signal to the sound processor unit 24 for use in the beamformer mode (this embodiment is indicated by dashed lines in FIG. 1). By providing such beamformer circuitry 80 in the microphone module 70, the sound processor unit 24 can be simplified, thereby requiring less complex circuitry to be included in the BTE housing 27.

According to an alternative embodiment, the beamforming algorithm is fully implemented in the sound processor unit 24, with the audio signal of each microphone 20A to 20E being supplied separately to the sound processor unit 24, as indicated by the solid lines in FIG. 1 (in this case there is no beamformer signal processing in the microphone module 70).

Preferably, the microphone module 70 is detachable from the BTE housing 27 in order to enable replacement of the microphone module 70, for example, in case of damage or degradation of one or several of the microphones of the microphone module 70.

The support element 72 of the microphone module 70 may be moved from the substantially horizontal beamformer position shown in FIG. 3 to the substantially vertical T-Mic position shown in FIG. 4 and back to the beamformer position by simple manual action by the patient.

According to one embodiment, the sound processor module 25 is adapted to determine the position of the support element 72 in order to automatically switch between the beamformer mode and the T-Mic mode based on the determined position of the support element 72. To this end, the microphone module 70 may comprise a sensor, for example an inclinometer/gravity sensor, in order to determine whether the support element 72 is in the beamformer position or in the T-Mic position. Typically, the beamformer mode is only used when the support element 72 is in the beamformer position, whereas the T-Mic mode typically is used only when the support element 72 is in the T-Mic position. Thereby, the patient may switch between the beamformer mode and the T-Mic mode and vice versa by simple manual action on the support element 72.

The sound processor module 25 may comprise a classifier unit (which may be functionally implemented in the sound processor unit 24) for determining a presently prevailing auditory scene by analyzing the input audio signals, as it is known in the art (for example, the classifier may determine that a single speaker in a noisy environment is speaking to the patient). The output of such classifier may be used, for example, to activate the beamformer mode once an auditory scene is detected in which beamforming is particularly helpful (for example, when the classifier found that there is a single speaker in a noisy environment); typically, such activation will be enabled only in case that the support element 72 is found to be in the beamformer position, since a beamformer mode would not be effective in the substantially vertical orientation of the support element 72 in the T-Mic position. Similarly, when the support element 72 is found to be in the T-Mic position, the T-Mic mode may be activated once an auditory scene has been detected in which the T-Mic mode is particularly helpful, such as the use of a telephone device; for example, it might be possible for the classier to select an optimal microphone for a particular telephone instrument or handset location.

Further, the sound processor unit 24 may automatically switch between a—more or less—tight beamformer mode and an omnidirectional mode, depending on the output of the classifier, when the support element 72 is in the beamformer position. In particular, an adaptive beamforming function may be implemented by using an adaptive beamforming algorithm in the beamformer mode which adapts the polar pattern of the beamforming according to the present auditory scene as determined by analyzing the input audio signals. For example, the polar pattern of the beamforming may be adapted to a noise field and/or a position of a target audio source, such as a speaker, as determined from analyzing the input audio signals. Such adaptive beamforming algorithm allows not only to implement end-fire arrays (forward and backward oriented) but also broad side arrays and other configurations, depending on the "look direction" of the patient and the position of the target source (such as a speaker).

In a bilateral system comprising a sound processor module at each of the patient's ears, a bilateral/binaural beamformer may be implemented in case that there is a wireless link between the two sound processor modules; in such system, a contralateral input audio signal captured by a microphone assembly/module of the contralateral sound processor module is received by the ipsilateral sound processor module and is utilized in a binaural beamforming algorithm together with the ipsilateral input audio signals. Thereby, their activity may be increased, compared to a monolateral beamformer.

According to one embodiment, the sound processor module 25 may be adapted to monitor the performance of each of the microphones 20A to 20E of the microphone module 70 by analyzing the respective input audio signals in order to disable/mute microphones having a performance below a given performance threshold.

It is to be understood that the invention may be used not only with auditory prostheses providing for neural stimulation only; rather, the invention also may be used with additional acoustic stimulation of the patient's residual hearing, namely bimodal systems (neural stimulation at one ear, acoustic stimulation at the other ear) and EAS systems (combined neural and acoustic stimulation at the same ear.

The invention claimed is:

1. A behind-the-ear (BTE) sound processor module for use in a device for neural stimulation of a patient's hearing, comprising:
   a BTE-housing to be worn behind an ear of the patient;
   an adjustable microphone module attached to the BTE-housing for capturing input audio signals from ambient sound;
   a sound processor unit for generating, from the input audio signals, a neural hearing stimulation signal to be supplied to an implantable neural stimulation arrangement,
   wherein the microphone module comprises a plurality of microphones and a support element for carrying the microphones, wherein the support element is movable between a first position enabling the plurality of microphones to act as a directional microphone array in a first audio signal processing mode of the sound processor unit and a second position enabling at least one of the microphones to act, in accordance with a second audio signal processing mode of the sound processor unit, as a microphone that is placed within a concha of an ear of the patient at a position closer to the entrance of the ear canal than in the first position.

2. The sound processor module of claim 1, wherein the microphone module is designed as an earhook.

3. The sound processor module of claim 1, wherein the microphone module is detachable from the BTE-housing in order to enable replacement of the microphone module.

4. The sound processor module of claim 1, wherein the microphone module includes circuitry for combining the output signals of the microphones according to a beamforming algorithm in order to supply a beamforming signal to the sound processor unit for use in the first audio signal processing mode.

5. The sound processor module of claim 1, wherein the microphones are arranged as a linear array.

6. The sound processor module of claim 1, wherein in the beamformer first position of the support element the microphones are arranged in a substantially horizontal plane having a deviation of less than 20° from the horizontal direction, when the sound processor module is worn by the patient.

7. The sound processor module of claim 1, wherein in the second position of the support element the microphones are arranged in a substantially vertical plane having a deviation of less than 30° from the vertical direction, when the sound processor module is worn by the patient.

8. The sound processor module of claim 1, wherein the support element is designed as an arm having a free end and having another end connected via a joint to an upper end of the BTE-housing.

9. The sound processor module of claim 8, wherein the support element is pivotable around the joint in plane substantially parallel to the pinna of the patient's ear, when the sound processor module is worn by the patient.

10. The sound processor module of claim 8, wherein the at least one microphone acting as the microphone that is placed within the concha of the ear of the patient is located at the free end of the support element.

11. The sound processor module of claim 10, wherein the at least one microphone acting as the microphone that is placed within the concha of the ear of the patient is oriented in an axial direction of the support element.

12. The sound processor module of claim 8, wherein in the second position the free end of the support element is located at the entrance of the ear canal, when the sound processor module is worn by the patient.

13. The sound processor module of claim 8, wherein in the second audio signal processing mode only the microphone closest to the free end of the support element is active or only the two microphones closest to the free end of the support element are active.

14. The sound processor module of claim 1, wherein in the first position at least two of the microphones are oriented downwardly, when the sound processor module is worn by the patient, said at least two microphones being located at a side of the support element which faces the floor in the first position.

15. The sound processor module of claim 1, wherein in the first position at least one of the microphones is oriented horizontally, when the sound processor module is worn by the patient, with a membrane of said at least one of the microphones being in a vertical plane in the first position.

16. The sound processor module of claim 1, wherein the sound processor module is adapted to determine the position of the support element and to automatically switch between the first audio signal processing mode and the second audio signal processing mode based on the determined position of the support element.

17. The sound processor module of claim 16, wherein the microphone module comprises a sensor for determining whether the support element is in the first position or in the second position.

18. The sound processor module of claim 1, wherein the sound processor module comprises a classifier for determining a present auditory scene by analyzing the input audio signals, and wherein the sound processor unit is adapted to automatically select an audio signal processing mode based on the determined auditory scene.

19. The sound processor module of claim 18, wherein in the first audio signal processing mode an adaptive beamforming algorithm is used which adapts the polar pattern of the beamforming according to the present auditory scene determined by the classifier.

20. The sound processor module of claim 19, wherein the polar pattern of the beamforming is adapted to a noise field and/or a position of a target audio source as determined by the classifier.

21. The sound processor module of claim 1, wherein the sound processor unit is adapted to automatically activate the first audio signal processing mode only when the support element is in the first position.

22. The sound processor module of claim 21, wherein the sound processor unit is adapted to automatically switch between the first audio signal processing mode and an omnidirectional mode when the support element is in the first position.

23. The sound processor module of claim 1, wherein the sound processor module is adapted to monitor the performance of each of the microphones by analyzing the input audio signals to disable microphones having a performance below a performance threshold.

24. The sound processor module of claim 1, wherein the sound processor module is adapted to receive, via a wireless link, a contralateral input audio signal captured by a microphone assembly of a sound processor module to be worn at the other ear of the patient, and to utilize such contralateral input audio signal in a binaural beamforming algorithm.

25. The sound processor module of claim 1, wherein the microphone module is attached to the BTE-housing via an adaptor.

26. A system for neural stimulation of a patient's hearing, comprising:
a behind-the-ear (BTE) sound processor module for use in a device for neural stimulation of a patient's hearing, comprising:
a BTE-housing to be worn behind an ear of the patient;
an adjustable microphone module attached to the BTE-housing for capturing input audio signals from ambient sound;
a sound processor unit for generating, from the input audio signals, a neural hearing stimulation signal to be supplied to an implantable neural stimulation arrangement,
wherein the microphone module comprises a plurality of microphones and a support element for carrying the microphones,
wherein the support element is movable between a first position enabling the plurality of microphones to act as a directional microphone array in a first audio signal processing mode of the sound processor unit and a second position enabling at least one of the microphones to act, in accordance with a second audio signal processing mode of the sound processor unit, as a microphone that is placed within a concha of an ear of the patient at a position closer to the entrance of the ear canal than in the first position.

27. The device of claim 26, wherein the neural stimulation arrangement is a cochlear implant stimulation arrangement comprising a plurality of electrodes for electrical stimulation of the cochlea.

* * * * *